United States Patent [19]
Yoon

[11] Patent Number: 5,531,761
[45] Date of Patent: Jul. 2, 1996

[54] METHODS FOR SUTURING TISSUE SECTIONS

[76] Inventor: Inbae Yoon, 2101 Highland Ridge Dr., Phoenix, Md. 21131

[21] Appl. No.: 144,590

[22] Filed: Oct. 28, 1993

Related U.S. Application Data

[60] Continuation of Ser. No. 855,053, Mar. 13, 1992, abandoned, which is a division of Ser. No. 744,406, Aug. 13, 1991, Pat. No. 5,222,976, which is a division of Ser. No. 352,337, May 16, 1989, Pat. No. 5,053,047.

[51] Int. Cl.$^6$ ................................................. A61B 17/04
[52] U.S. Cl. ........................... 606/223; 606/226; 606/230
[58] Field of Search ............................... 606/213–221, 606/139, 898, 223–230; 128/898

[56] References Cited

U.S. PATENT DOCUMENTS

| | | |
|---|---|---|
| 1,293,660 | 2/1919 | Armstrong . |
| 1,377,359 | 5/1921 | Littlejohn . |
| 2,413,142 | 12/1946 | Jones et al. . |
| 2,715,486 | 8/1955 | Marloff-Moghadam et al. . |
| 2,883,096 | 4/1959 | Dawson . |
| 3,123,077 | 3/1964 | Alcamo . |
| 3,166,072 | 1/1965 | Sullivan . |
| 3,206,086 | 9/1965 | Duffney . |
| 3,212,502 | 10/1965 | Myers . |
| 3,233,800 | 2/1966 | Catania . |
| 3,249,104 | 5/1966 | Hohnstein . |
| 3,412,912 | 11/1968 | Rosenberg . |
| 3,570,497 | 3/1971 | Lemole . |
| 3,739,773 | 6/1973 | Schmitt et al. . |
| 3,797,499 | 3/1974 | Schneider . |
| 3,827,277 | 8/1974 | Weston . |
| 3,880,167 | 4/1975 | Hardwick . |
| 4,006,747 | 2/1977 | Kronenthal et al. . |
| 4,060,089 | 11/1977 | Noiles . |
| 4,069,825 | 1/1978 | Akiyama . |
| 4,141,087 | 2/1979 | Shalaby et al. . |
| 4,182,341 | 1/1980 | Perri . |
| 4,300,565 | 11/1981 | Rosensaft et al. . |
| 4,429,080 | 1/1984 | Casey et al. . |
| 4,490,326 | 12/1984 | Beroff . |
| 4,510,934 | 4/1985 | Batra . |
| 4,513,746 | 4/1985 | Aranyi et al. . |
| 4,523,591 | 6/1985 | Kaplan et al. . |
| 4,532,926 | 8/1985 | O'Holla . |
| 4,548,202 | 10/1985 | Duncan . |
| 4,573,469 | 3/1986 | Golden et al. . |
| 4,590,937 | 5/1986 | Deniega . |
| 4,595,007 | 6/1986 | Mericle . |
| 4,602,634 | 7/1986 | Barkley . |
| 4,646,741 | 3/1987 | Smith . |
| 4,649,921 | 3/1987 | Koelmel et al. . |
| 4,671,280 | 6/1987 | Dorband et al. . |
| 4,719,917 | 1/1988 | Barrows et al. . |
| 4,741,337 | 5/1988 | Smith et al. . |
| 4,744,365 | 5/1988 | Kaplan et al. . |
| 4,832,026 | 5/1989 | Jones . |
| 4,873,976 | 10/1989 | Schreiber . |
| 4,901,721 | 2/1990 | Hakki .................... 606/103 |
| 4,932,962 | 6/1990 | Yoon ...................... 606/224 |
| 4,935,028 | 6/1990 | Drews . |
| 4,936,835 | 6/1990 | Haaga .................... 604/265 |
| 4,950,285 | 8/1990 | Wilk ....................... 606/232 |
| 4,979,954 | 12/1990 | Gwathney et al. ...... 606/219 |
| 4,981,149 | 1/1991 | Yoon . |
| 4,997,436 | 3/1991 | Oberlander ............. 606/142 |
| 5,002,562 | 3/1991 | Oberlander ............. 606/224 |
| 5,074,874 | 12/1991 | Yoon ...................... 606/224 |

FOREIGN PATENT DOCUMENTS

| | | |
|---|---|---|
| 2651113 | 3/1991 | France . |
| 213834 | 9/1984 | Germany . |
| 8603396 | 6/1976 | WIPO . |

*Primary Examiner*—Gary Jackson

[57] ABSTRACT

Suture devices, particularly useful in endoscopic surgery, include a suture device made of bioabsorbable material having an elongate body member with a sharp distal end for penetrating tissue and means for locking the suture device in tissue to prevent forward and rearward movement and a suture device made of bioabsorbable material having a hinge-like joint for folding a distal portion at a precise location to be juxtaposed with a proximal portion for adjustable locking. Methods of using the suture devices for joining tissue sections, such as in tuboplasty, for closing anatomical lumens and for subcuticular suturing.

12 Claims, 2 Drawing Sheets

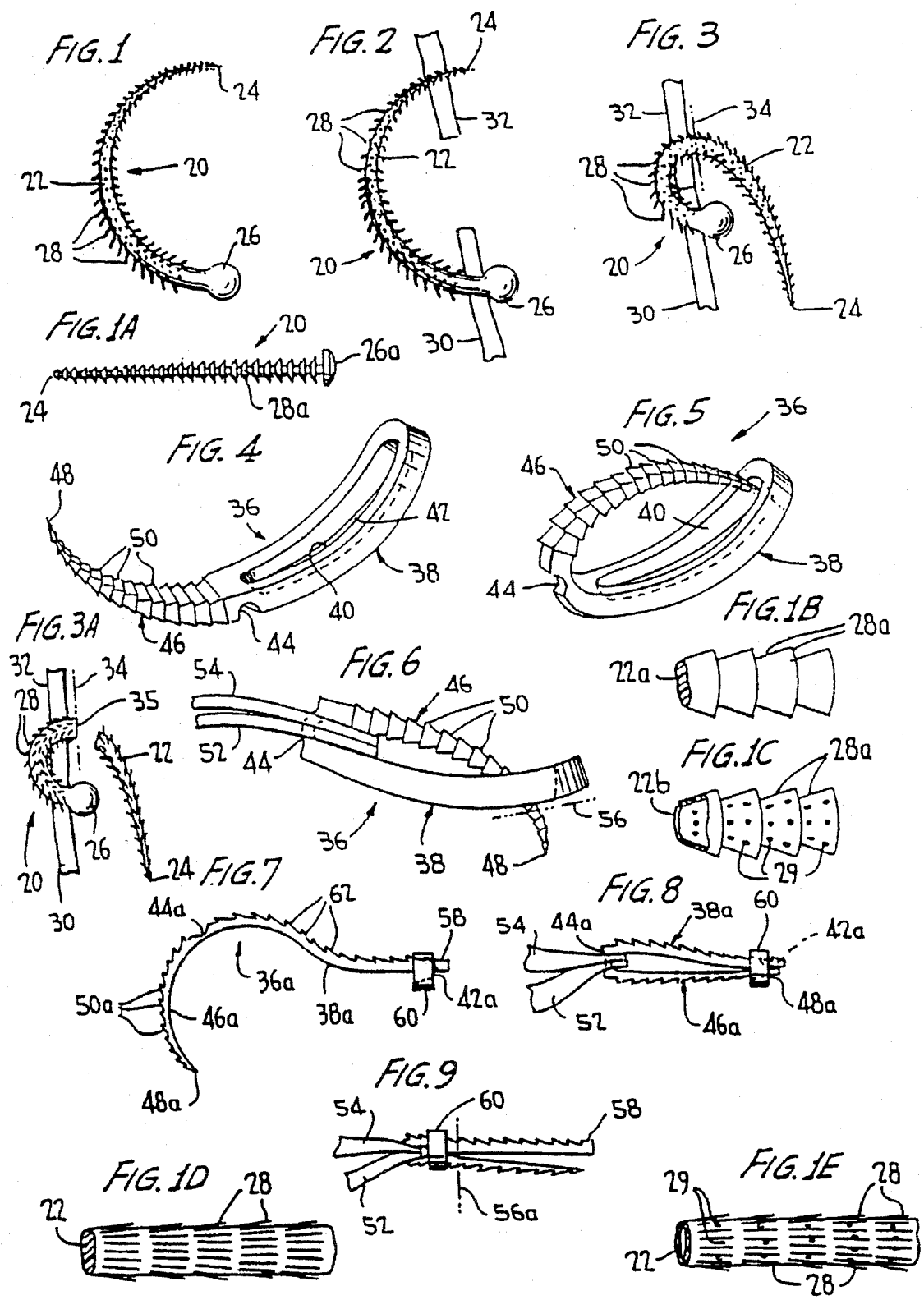

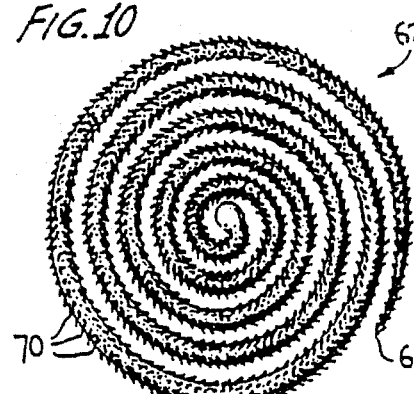
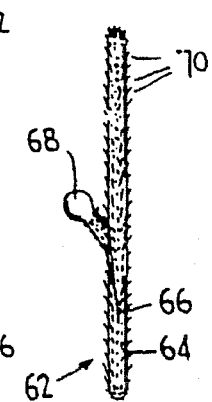
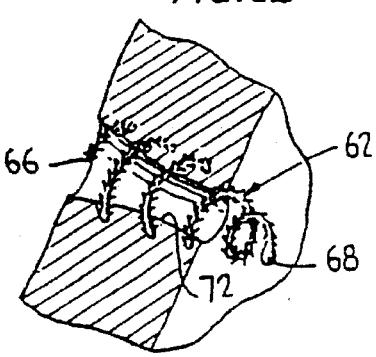
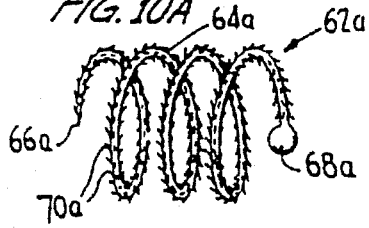
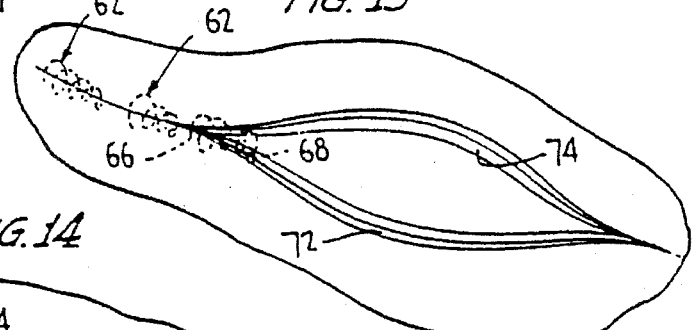
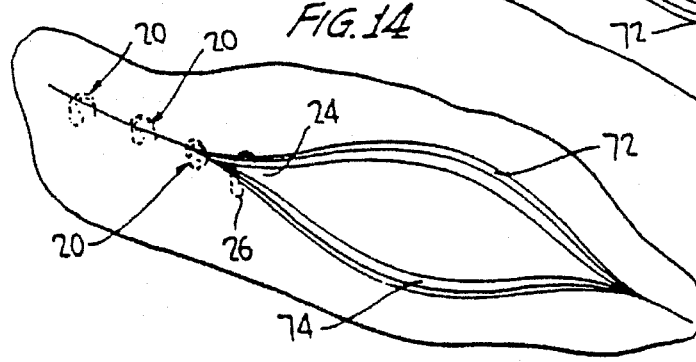
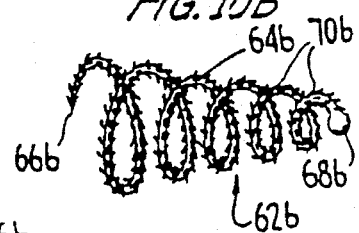
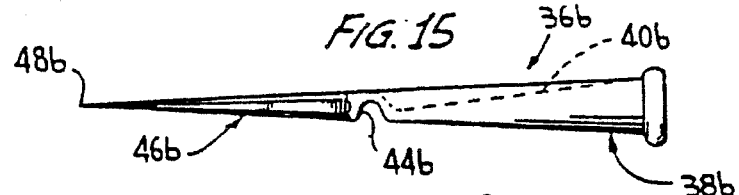
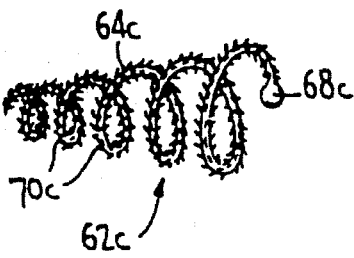
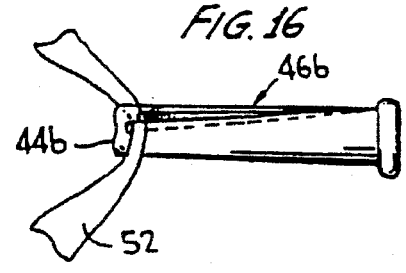

METHODS FOR SUTURING TISSUE SECTIONS

This application is a continuation of application Ser. No. 07/855,053, filed Mar. 13, 1992, now abandoned which is a division of application Ser. No. 07/744,406 filed Aug. 13, 1991, now U.S. Pat. No. 5,222,976 which is a division of application Ser. No. 07/352,337 filed May 16, 1989, now U.S. Pat. No. 5,053,047.

BACKGROUND OF THE INVENTION

1. Field of the Invention

The present invention relates to surgical suture devices and, more particularly, to suture needle-like suture devices made of bioabsorbable materials particularly useful in endoscopic surgery and methods of suturing using such suture devices.

2. Discussion of the Prior Art

Suturing of bodily tissue is a time consuming part of most surgical procedures including both open surgery and endoscopic or closed surgery. By open surgery is meant surgery wherein the surgeon gains access to the surgical site via a relatively large incision, and by endoscopic surgery is meant surgery wherein the surgeon gains access to the surgical site via one or more portals through which endoscopes are introduced to view the surgical site and through which instruments, such as forceps, cutters, applicators and the like, are introduced to the surgical site. There are many common endoscopic surgical procedures, including arthroscopy, laparascopy (pelviscopy), gastroentroscopy and laryngobronchoscopy, for example. In the past, suturing has been accomplished with the use of a sharp metal suture needle attached to the end of a length of suture material, the suture needle being caused to penetrate and pass through the tissue pulling the suture material through the tissue. Once the suture material has been pulled through the tissue, the surgeon ties a knot in the suture material, the knotting procedure allowing the surgeon to adjust the tension on the suture material to accommodate the particular tissue being sutured and control approximation, occlusion, attachment or other conditions of the tissue. The ability to control tension is extremely important to the surgeon regardless of the type of surgical procedure being performed; however, knotting of the suture material is time consuming and tedious work, particularly in microsurgery and endoscopic surgery. That is, in microsurgery suturing is necessarily time consuming due to the small size of the suture needle and the suture material and the concomitant difficult manipulation required to pass the suture needle through the tissue and to tie a knot in the suture material. With respect to endoscopic surgery, suturing and tying knots represents an even more time consuming procedure due to the difficult maneuvers required. Accordingly, while endoscopic surgery would be preferred for most procedures, the advantages are often outweighed by the disadvantages caused by the length of time required to complete the endoscopic surgical procedure, which time is greatly extended due to the time required for suturing. Another disadvantage of suturing with a metal suture needle and suture material during endoscopic surgery is that the suture needle is difficult to hold and manipulate and can be easily dropped. Should the suture needle be dropped, open surgery with its attendant disadvantages must be performed to find and remove the needle.

There have been many attempts to provide devices to take the place of conventional suturing with a suture needle and a length of suture material; however, such prior art devices have essentially been staples, clips, clamps or other fasteners not providing the adjustable tension obtained by the surgeon while knotting a length of suture material. U.S. Pat. Nos. 3,827,277 to Weston, 4,060,089 to Noiles, 4,490,326 to Beroff et al, 4,513,746 to Aranyi et el, 4,532,926 to O'Holla, 4,548,202 to Duncan, 4,573,469 to Golden, 4,590,937 to Deniega, 4,595,007 to Meride, 4,602,634 to Barkley, 4,646,741 to Smith, 4,671,280 to Dorband et al, 4,719,917 to Barrows et al and 4,741,337 to Smith et al are representative of such prior art devices for use in place of conventional suturing. Many of these prior art devices are made of bioabsorbable materials such that the devices are absorbed over time into the bodily tissue and do not have to be removed after the bodily tissue has healed.

There exist many compositions useful as bioabsorbable materials, as represented by the above patents and by U.S. Pat. Nos. 3,739,773 to Schmitt et al, 3,797,499 to Schneider, 4,141,087 to Shalaby et al, 4,300,565, 4,523,591 to Kaplan et al and 4,649,921 to Koelmel et al which discuss characteristics of various bioabsorbable materials and medical devices desirably manufactured of such materials, such medical devices being of a type designed to be engaged in, embedded in or otherwise attached to various types of bodily tissue, such as bone, muscle, organs, skin and other soft tissue, to remain in place in the tissue until the device is absorbed into the body.

U.S. Pat. No. 3,570,497 to Lemole discloses a suture device formed of a needle with a piercing point extending from a latch cord carrying notches designed to pass through a latch collar, the latch cord being resilient to be curved upon itself to form a suture stitch without requiring tying of a knot; however, the latching function does not provide the same feel and tension control as knotting a length of suture material. U.S. Pat. No. 4,548,202 to Duncan uses similar structure in a tissue fastener device in that serrations or angled barbs are provided on spaced legs passing through tissue to be engaged by an apertured receiver or a flexible filament mesh. U.S. Pat. No. 3,123,077 to Alcamo discloses a surgical suture carrying raised projections or depressions or teeth such as barbs or spicules to snag or penetrate tissue to effectively hold a sewed incision or wound.

Endoscopic surgery is preferred over open surgery due to the greatly reduced trauma and wound healing time for the patient and due to concomitant cost savings associated with shorter hospital stays and performing surgery without general anesthesia and in non-hospital or out-patient surgery sites. Accordingly, there has been much effort spent to develop techniques for facilitating the suturing normally performed by use of a metal suture needle and a length of suture material. Alternative techniques proposed have included electrical coagulation, mechanical devices such as clips, clamps and staples, and lasers; however, no well accepted alternative has yet been found in that suturing and tying are essential and vital parts of most surgical procedures. That is, to date the proposed alternatives have had disadvantages, including increased risk to the patient, while not providing the surgeon with the advantages of suturing and tying and not being useful in a wide range of procedures to allow expansion of the areas in which endoscopic surgery can be effectively performed. Thus, there is a great need for suture devices, particularly useful in endoscopic surgery, that allow surgeons to suture and tie knots in a manner with which they are familiar without undue concern as to the loss of the suture needle and further for suture devices that allow controlled approximation of tissue and tying to produce controlled tension.

SUMMARY OF THE INVENTION

Accordingly, it is a primary object of the present invention to provide suture devices particulary useful in endoscopic surgery overcoming the above mentioned disadvantages of the prior art.

Another primary object of the present invention is to construct a suture device having characteristics similar to a suture needle such that a surgeon can manipulate the suture device to penetrate tissue using techniques similar to those used for suturing with a suture needle and a length of suture material.

A further object of the present invention is to provide a suture needle-like suture device in the form of a body member made of bioabsorbable material having an enlarged proximal end, a sharp distal end and protrusions therebetween configured such that the suture device can be inserted through tissue in only a forward direction and locked in the tissue with forward movement limited by the enlarged proximal end and rearward movement limited by the protrusions which can be whisker-like filaments angled away from the sharp distal end toward the enlarged proximal end. Any portion of the distal end of the needle protruding from the tissue can be cut off and removed.

An additional object of the present invention is to provide a suture needle-like suture device for joining bodily tissue having a distal portion terminating at a sharp tip and a proximal portion hingedly connected with the distal portion such that the distal portion can penetrate the tissue and be folded or bent at the hinge to a position juxtaposed with the proximal portion with the sharp tip received in an opening carried by the proximal portion to be adjustably locked therein.

Another object of the present invention is to provide a method of suturing an opening in skin by penetrating the subcutaneous fat layer with suture needle-like suture devices made of bioabsorbable material and movable only in a forward direction to approximate the opposite sides of the opening.

The present invention has another object in the use of a suture needle-like suture device made of bioabsorbable material and having a coiled configuration in a method of closing an anatomical lumen.

A further object of the present invention is to provide a suture needle-like suture device made of bioabsorbable material that can be locked in tissue to prevent both forward and rearward movement.

An additional object of the present invention is to position a hinge-like joint on a suture needle-like suture device made of bioabsorbable material such that a distal portion of the suture device can be folded at a precise location after penetration of tissue to be juxtaposed with a proximal portion of the suture device to facilitate use of the suture device to produce desired adjustable locking of the distal and proximal portions.

A further object of the present invention is to configure suture needle-like suture devices made of bioabsorbable material to allow a knotting function to be produced similar to tying a knot in a length of suture material during conventional suturing.

The present invention is generally characterized in a suture needle-like suture device made of bioabsorbable material including an elongate body member having a sharp distal end for penetrating tissue and carrying means for locking the suture device in tissue to prevent forward and rearward movement, a suture needle-like suture device made of bioabsorbable material having a hinge-like joint for folding a distal portion at a precise location to be juxtaposed with a proximal portion for adjustable locking, and methods of using the suture devices for joining and approximating tissue, for closing anatomical lumens and for subcuticular suturing.

Some of the advantages of the present invention over the prior art are that surgeons can easily and quickly utilize the suture devices during endoscopic surgery to approximate and join tissue without intricate manipulations and to provide suture stitches in a short time since the suture devices have configurations and characteristics to permit manipulation thereof in a manner similar to suture needles, endoscopic surgery can be used for additional procedures due to the reduced time required for suturing coupled with the knotting function provided by the suture devices, and the suture devices can replace conventional suturing with a length of suture material while providing all of the advantages thereof desired by surgeons.

Other objects and advantages of the present invention will become apparent from the following description of the preferred embodiments taken in conjunction with the accompanying drawings.

BRIEF DESCRIPTION OF THE DRAWINGS

FIG. 1 is a side view of a suture device according to the present invention.

FIG. 1A is a side view of a modification of the suture device of FIG. 1.

FIG. 1B and 1C are broken views of the body member of the suture device of FIG. 1A.

FIGS. 1D and 1E are broken views of the body member of the sutue device of FIG. 1.

FIGS. 2, 3 and 3A are side views showing use of the suture device of FIG. 1.

FIG. 4 is a perspective view of another embodiment of a suture device according to the present invention.

FIG. 5 is a perspective view of the suture device of FIG. 4 in a bent configuration.

FIG. 6 is a side view showing use of the suture device of FIG. 4.

FIG. 7 is a side view of a further embodiment of a suture device according to the present invention.

FIGS. 8 and 9 are side views showing use of the suture device of FIG. 7.

FIG. 10 is a side view of another embodiment of a suture device according to the present invention.

FIGS. 10A, 10B and 10C are side views of modifications of the suture device of FIG. 10.

FIG. 11 is an end view of the suture device of FIG. 10.

FIG. 12 is a perspective view showing use of the suture device of FIG. 10.

FIG. 13 is a perspective view showing another use of the suture device of FIG. 10.

FIG. 14 is a perspective view showing another use of the suture device of FIG. 1.

FIG. 15 is a side view of an additional embodiment of a suture device according to the present invention.

FIG. 16 is a side view showing use of the suture device of FIG. 15.

DESCRIPTION OF THE PREFERRED EMBODIMENTS

A suture needle-like suture device 20 according to the present invention is illustrated in FIG. 1 and includes an elongate, curved body member 22 having a sharp distal end 24 for penetrating tissue in a manner similar to a suture needle and a bulbous enlarged proximal end 26, the elongate, curved body member 22, having a round shape in cross-section and gradually tapering from proximal end 26 to sharp distal end 24. Angled, whisker-like filaments 28 extend from the body member 22 rearwardly toward proximal end 26 and are positioned around the body member and along the length thereof. The suture device 20 is made of bioabsorbable material and is intended to remain in the tissue to be absorbed therein.

The use of suture device 20 is illustrated in FIGS. 2 and 3 wherein a section of tissue 30 is to be joined to a section of tissue 32. The tissue can be of any configuration from any anatomical part or organ of the body; however, the suture device 20 is particularly useful for various anastomosis or approximating procedures such as vascular anastomosis, bowel anastomosis, closure of anatomical or non-anatomical structures, tuboplasty and skin closure. Due to the smoothly angled orientation of the whisker-like filaments 28, the suture device can penetrate through the tissue in only the forward direction and cannot be moved rearwardly. The sharp distal end 24 is moved to penetrate through tissue section 30 at a position spaced from the end of the tissue section in a manner similar to movement of a suture needle and is thereafter moved to penetrate through tissue section 32 at a position spaced from the end of tissue section 32. The suture device is manipulated with a conventional needle holder in a manner similar to a suture needle and can be easily utilized during endoscopic surgery; and, once the suture device has been positioned as illustrated in FIG. 2, the distal end is gasped and pulled thereby approximating the ends of the tissue sections 30 and 32 as illustrated in FIG. 3, it being noted that the enlarged bulbous proximal end 26 prevents the suture device from pulling through tissue section 30 since the proximal end has a dimension in at least one direction transverse to the body member greater than the transverse dimension of the body member. Once the suture device is in the position illustrated in FIG. 3 with the ends of the tissue sections approximated, the portion of the suture device protruding from tissue section 32 is severed as shown at line 34 leaving the suture device in the tissue. The suture device will remain in position since the angled, whisker-like filaments will not allow the suture device to move rearwardly and the enlarged bulbous proximal end 26 will not allow the suture device to move forwardly. Additionally, by using a shearing cutting device to sever the protruding distal portion of the suture device, the cut end can be expanded to form a flange 35 to further prevent rearward movement of the suture device. A number of suture devices 20 may be required to provide a complete suturing procedure; and, for anastomosis or tuboplasty, as many as four, five or six suture devices may be used dependent upon the size of the tubular structure and the thickness of the wall thereof. The suture device will be absorbed in the tissue after joining and healing of the ends of the tissue sections.

By providing body member 22 with an arcuately and smoothly curving configuration, the suture device 20 can be made of a rigid bioabsorbable material in that pulling the suture device through tissue section 32 causes the suture device to essentially pivot about the proximal end 26 to move tissue section 32 to abut tissue section 32. It will be appreciated, however, that suture device 20 can have other configurations and can be made of bioabsorbable materials of varying flexibility or rigidity for use with particular anatomical tissues. For example, suture device 20 can be straight, or rectilinear, as shown in FIG. 1A at 20a, and made of flexible bioabsorbable material to allow the body member 22 to bend as it is drawn through tissue section 32 to approximate the edges of the tissue sections. The proximal end 26 can have any desired configuration to prevent forward movement of the suture device once the suture device has passed through the initial tissue section; for example, the enlarged proximal end could have a flat, nail head-type shape, as shown at 26a in FIG. 1A, or the proximal end could have angled, whisker-like filaments extending forwardly therefrom toward the sharp distal end. The body member can have a uniform diameter therealong with a tapered sharp distal end and can have various cross-sectional configurations and be either solid or hollow. The whisker-like filaments are preferred to provide the function of permitting only forward movement of the suture device through the tissue, or, in other words, preventing reverse movement of the suture device; however, the body member can carry other means of permitting only forward movement such as protrusions of various configurations. By providing the whisker-like filaments along the length of the body member, the suture device 20 provides a knotting function similar to tying a knot in a length of suture material. That is, compression and approximation of the tissue sections can be variably controlled in accordance with the tension applied to the suture device as it is pulled through the tissue by grasping the distal end 24.

The suture device 20a has rearwardly angled protrusions 28a having a truncated conical configuration to permit only forward movement of the suture device, in place of whisker-like filaments 28, the protrusions being shown in FIG. 1B with a solid body member 22a and in FIG. 1C with a hollow body member 22b. When the body member is hollow, the interior lumen can be filled with various pharmacological agents by constructing the proximal end to be detachable, such as by screw threads or a friction fit, and microholes 29 extend radially through the body member to communicate with the lumen and provide passages for the pharmacological agents to leach out into the suture site. As previously noted, the use of whisker-like or hair-like filaments to permit only forward movement of the suture device is preferred in that, as shown in FIGS. 1D and 1E, the filaments lay against body member 22 as the suture device is moved forwardly to penetrate tissue producing minimal obstruction to smooth movement. However, any tendency for the suture device to move rearwardly causes the filaments to protrude, as shown in FIG. 1, to lock the suture device in the tissue. The body member 22 in FIG. 1D is solid while the body member in FIG. 1E is hollow to allow the interior lumen to be filled with a pharmacological agent for leaching into the suture site.

Another embodiment of a suture device according to the present invention is illustrated in FIG. 4. The suture needle-like suture device 36 is integrally formed of bioabsorbable material and includes a proximal portion 38 having an opening 40 therein defining a bottom edge 42 tapering from a small width at the proximal end to be progressively wider. The body of the proximal portion 38 is relatively thick and terminates at a transversely extending recess 44 which forms a hinge-like joint defining a precise bending point from which extends a distal portion 46 tapering to a sharp, suture needle-like point 48 at the distal end of the suture device. A plurality of tapered barbs 50 extend along the distal portion 46 and, as illustrated, have truncated, tetrahedral, pyramidal shapes while other shapes could be provided as will be understood from the following discussion of the engagement of the barbs with the bottom edge 42 of the opening 40 in the proximal portion 38. For example, whisker-like filaments can protrude from the distal portion for engaging the proximal portion. The recess 44 allows the suture device 36 to be bent or folded about the transverse axis thereof, as illustrated in FIGS. 5 and 6, such that the proximal portion 38 and the distal portion 46 can be juxtaposed. The proximal portion 38 has a concave curved configuration and the distal portion 46 has a similar curved configuration such that, when the suture device 36 is bent of folded on itself at recess 44, the opposing ends of the suture device extend in opposite directions.

In use, the sharp point 48 is moved to penetrate sections of tissue 52 and 54 to be sutured to approximate sections of tissue until recess 44 is positioned adjacent the tissue to limit further movement of the suture device, it being noted that the enlarged size of the proximal portion limits penetration in the tissue. The distal portion 46 is then folded in a hinge-like manner about the recess 44, and the sharp distal end 48 is passed through the opening 42 in the proximal portion such that the suture device 36 now has the configuration illustrated in FIG. 5. The proximal and distal portions of the suture device are now forced towards one another such that the sharp distal end 48 passes through the opening 42 to protrude from the bottom as shown in FIG. 6. The distal end 48 can be pulled to adjustably tighten the suture device to provide a knotting function similar to tying a knot in a length of suture material with the barbs 50 engaging the bottom edge 42 of the opening 40 to lock the distal portion in place. The protruding portion of the distal end of the suture device can be severed as shown at line 56. The suture device 36 will thus hold the tissue in approximated position until the tissue is joined after which the suture device 36 will be absorbed in the body.

A modification of the suture device of FIG. 4 is illustrated in FIG. 7 and similar reference numbers with an "a" added are used to identify similar parts. The suture device 36a is made of flexible bioabsorbable material and includes a proximal portion 38a having a proximal end 58 around which is mounted a ring or ring-like member 60 having an opening 42a therethrough with a conical or tapered inner surface defining a locking edge 42a. A transversely extending recess 44a defines a hinge-like joint at the end of the proximal portion 38a, and a distal portion 46a extends from recess 44a and tapers to a sharp, suture needle-like, distal end 48a. Barbs 50a protrude from distal portion 46a angled in a direction away from distal end 48a while a plurality of similar barbs 62 protrude from proximal portion 38a in a direction toward distal end 48a such that the barbs 50a and 62 are angled toward each other prior to use of the suture device, as shown in FIG. 7, but are angled in the same direction when the suture device is bent or folded about recess 44a. The inner surfaces of proximal portion 38a and distal portion 46a are smooth or longitudinally ribbed or grooved to abut and/or lock one another when the suture device is bent at recess 44a.

In use, the sharp distal end 48a is moved to penetrate sections of tissue 52 and 54 to be sutured to approximate the sections of tissue, and the distal portion 46a is pulled through the tissue to position recess 44a adjacent the tissue as shown in FIG. 8. The distal portion is then folded in a hinge-like manner about the recess 44a such that the proximal and distal portions are juxtaposed with the sharp distal end 48a received in the opening 42a in ring 60. The ring 60 is then moved toward the joint (to the left looking at FIGS. 8 and 9), it being appreciated that the inner surface of opening 42a tapers away from the joint such that the ring can move in only a direction toward the joint. As best shown in FIG. 9, the ring is moved in a manner similar to a knot during conventional suturing with a length of suture material until the ring is positioned as desired; and, once the ring has been properly positioned, the protruding proximal and distal portions are severed as indicated at 56a.

Suture devices 36 and 36a can have various configurations and sizes dependent upon the specific tissue to be sutured, it being important that the suture devices have a well defined bending or folding joint such that the distal portion can be folded in a hinge-like manner after penetration of the tissue to be juxtaposed along the proximal portion and engaged or interlocked with the proximal portion in an adjustable manner to provide a knotting function similar to tying knots with a length of suture material. While the distal portion is adjustably locked in an opening carried by the proximal portion in suture devices 36 and 36a, other adjustable locking means could be used as long as operation thereof can be simply effected to facilitate use. By providing a precise bending position, use of the suture devices by the surgeon is facilitated and standardized allowing the surgeon to simply reproduce the knotting function on a plurality of stitches. Preferably, the suture devices are made of bioabsorbable materials having a hardness and rigidity increasing from the joint toward the proximal and distal ends, and the ring 60 is made of rigid bioabsorbable material.

Another embodiment of a suture needle-like suture device 62 according to the present invention is illustrated in FIG. 10 and includes an elongate body member 64 terminating at a sharp distal end 66 for penetrating tissue in a manner similar to a suture needle and at a bulbous enlarged proximal end 68, the elongate body member having a spiral configuration with the coils disposed in a single plane and having a round shape in cross-section. Angled, whisker-like filaments 70 extend from the body member rearwardly toward proximal end 26 and are positioned around the body member and along the length thereof such that the suture device 62 can pass through tissue in only a forward direction. The suture device is made of flexible, resilient bioabsorbable material such that the suture device contracts after insertion in tissue to be sutured attempting to return to its pre-suturing shape; and, accordingly, the suture device is particularly effective for closing anatomical lumens and subcuticular suturing. The spiral or coiled configuration can also circle about a central axis in curves of conical form, as shown in FIGS. 10 and 10D, or cylindrical form, as shown in FIG. 10B, dependent upon the particular use of the suture device; and, as noted above with respect to suture device 20, the proximal end can have any desired configuration, the cross-section of the body member can vary and the body member can carry other means of permitting only forward movement of the suture device. Additionally the proximal end 68 can be transposed with the sharp distal end 66 such that the coils become smaller as they approach the distal end. The suture devices shown in FIGS. 10A, 10B and 10C have expanded pre-suturing states, and the coils in FIG. 10A have the same diameter while the diameter of the coils in FIG. 10B increase as they approach the distal end and the diameter of the coils in FIG. 10C decrease as they approach the distal end. Parts of the suture devices 62a, 62b and 62c of FIGS. 10A, 10B and 10C, respectively, are given reference number the same as similar parts of suture device 62 with "a", "b", or "c" added, and the following description of use pertains to suture devices 62, 62a, 62b and 62c.

One use of suture device 62 is shown in FIG. 12 wherein an anatomical lumen 72 in tissue is closed by penetrating the surrounding tissue with the sharp distal end 66 and rotating or screwing the suture device into the tissue until proximal end 68 abuts the tissue. The suture device will be locked in place since forward movement is prevented by proximal end 68 and rearward movement is prevented by the whisker-like filaments 70, and the spiral configuration will close the lumen.

Use of the suture device 62 for subcuticular suturing is shown in FIG. 13 wherein the tissue to be sutured is skin having an outer layer 74 formed of the epidermis and the germinal epithelium and a subcutaneous layer of fat 76 primarily formed of collagen. By penetrating the subcutaneous layer 76 only, and not the outer layer 74, with a series of suture devices 62, a wound or opening in the skin can be closed to facilitate healing and minimize scar tissue. The sharp distal end 66 of the suture device is moved to penetrate the subcutaneous layer 74 where the first stitch is to be taken, and the suture device is rotated to cause the suture device to advance into the subcutaneous layer until the enlarged proximal end 68 engages the tissue at which point the suture device will be locked in place with the two sides of the wound held in close engagement for healing while the suture device is absorbed in the tissue. Thus, suture device 62 can be simply manipulated by a surgeon to close a wound by subcutaneously suturing in a time efficient manner.

FIG. 14 illustrates use of suture device 20 of FIG. 1 for subcutaneous suturing, a series of the suture devices 20 being used in a manner similar to that described above with respect to suture device 62 with the exception that only a single bite of tissue is taken with each suture device 20 as compared with the multiple bites taken With each suture device 62. The number of coils in the suture device determines the number of bites taken thereby; and, thus, it will be appreciated that the number of coils can vary as desired, suture device 20 providing one bite while suture device 62 provides five bites or stitches.

A modification of the hinge-like foldable suture devices 36 and 36a of FIGS. 4 and 7, respectively, is illustrated in FIG. 15 wherein similar parts are given similar reference numbers with a "b" added. The suture device 36b of FIG. 15 is integrally formed of bioabsorbable material and includes a proximal portion 38b having an opening 40b therein, the proximal portion 38b terminating at a transversely extending recess 44b forming a hinge-like joint defining a precise bending point from which extends a distal portion 46b tapering to a sharp, suture needle-like point 48b at the distal end of the suture device. The opening 40b is formed of a tapering recess becoming gradually deeper and wider as it approaches the hinge-like joint. The width of the recess 40b is slightly less than the corresponding width of the distal portion 46b of the suture device when the suture device is folded to juxtapose the proximal and distal portions. The distal portion 46b gradually tapers to sharp distal point 48b and is faceted. Use of the suture device 36b is illustrated in FIG. 16 for suturing tissue 52, for example to occlude a tubular body part or organ. The tissue is penetrated with the sharp distal portion 46b and then folded at recess 44b to juxtapose the distal and proximal portions as shown. The distal portion 44b can then be depressed into the recess opening 40b in an adjustable manner corresponding to the tissue being sutured, the plastic nature of the bioabsorbable material holding the distal portion within the proximal portion.

Various bioabsorbable or biodegradable materials can be used to make the suture devices of the present invention with the composition determined by the rigidity or flexibility required. Generally, the bioabsorbable materials are thermoplastic polymers, such as absorbable polymers and copolymers of polydioxanne, lactide, glycolide and the like. Polyglycolic acid is disclosed in U.S. Pat. Nos. 3,463,158; 3,739,773 and 3,772,420. Suitable polylactic acids are disclosed in U.S. Pat. No. 3,636,956. Examples of absorbable polyesters are shown in U.S. Pat. Nos. 3,225,766 and 3,883,901. Absorbable cellulose glycolic acid ethers are shown in U.S. Pat. No. 2,764,159. Examples of suitable esters of alpha-cyanoacrylic acid are found in U.S. Pat. Nos. 3,527,841, 3,564,078 and 3,759,264.

From the above, it will be appreciated that the suture devices according to the present invention have configurations to allow the suture devices to be handled or manipulated by surgeons in a manner similar to conventional suture needles. That is, the surgeon will grasp the proximal end of the suture device, for example with a needle holder, and move the suture needle to penetrate the tissue. The suture devices can be placed in the tissue in a manner to control and adjust the tension on the suture device or the compression of the tissue to produce a knotting function in an efficacious manner easily accomplished by the surgeon such that suturing and knotting can be quickly performed during endoscopic surgery.

Inasmuch as the present invention is subject to various modification and changes in detail, the above description of a preferred embodiment is intended to be exemplary only and not limiting.

What is claimed:

1. A method of suturing first and second tissue sections comprising the steps of penetrating an external wall of the first tissue section at a position closely spaced from the end thereof with a sharp distal end of a suture device made of bioabsorbable material and having protrusions therealong, including protrusions immediately adjacent the sharp distal end, for permitting movement of the suture device only forwardly through the tissue sections such that the sharp distal end passes through an internal wall of the first tissue section;

penetrating an internal wall of the second tissue section at a position closely spaced from the end thereof with the sharp distal end of the suture device such that the sharp distal end protrudes from an external wall of the second tissue section;

pulling the protruding sharp distal end of the suture device to move the suture device forwardly through the first and second tissue sections to approximate the ends thereof; and leaving the suture device in the first and second tissue sections to allow joining of the ends thereof prior to absorption of the suture device.

2. A method as recited in claim 1 wherein said tissue sections are tubular and further comprising repeating said penetrating and pulling steps to place a plurality of suture devices in the first and second tubular tissue sections.

3. A method as recited in claim 2 and further comprising the steps of severing the protruding sharp distal ends of the suture devices.

4. A method as recited in claim 1 and further comprising the step of severing the protruding sharp distal end of the suture device.

5. A method of closing an anatomical lumen comprising the steps of penetrating tissue surrounding the lumen with a sharp distal end of a suture device made of bioabsorbable material and having a coiled configuration;

rotating the suture device into the surrounding tissue to cause the coils of the suture device to extend around the lumen to contract the walls of the lumen; and leaving the suture device in the surrounding tissue to be absorbed.

6. A method of suturing an opening in skin comprising the steps of penetrating a subcutaneous layer of the skin on one side of the opening with a sharp distal end of a suture device made of bioabsorbable material having a coiled configuration and having means for permitting movement of the suture device only forwardly through the subcutaneous layer;

rotatably moving the suture device forwardly in a curving path to cause the sharp distal end to penetrate the subcutaneous layer of the skin on the other side of the opening to approximate the sides of the opening; and leaving the suture device in the subcutaneous layers to allow joining of the skin prior to absorption of the suture device.

7. A method of suturing tissue comprising the steps of providing a suture device made of bioabsorbable material and including a flexible body having a distal portion terminating distally at a sharp distal end, a proximal portion terminating proximally at a proximal end, and a straight configuration extending between the sharp distal end and the proximal end, the body being configured to permit movement of the suture device only forwardly through the tissue;

penetrating the tissue with the sharp distal end of the suture device;

advancing the suture device forwardly in a straight path into the tissue to cause the body and the proximal end of the suture device to follow the sharp distal end to position a portion of the body in the tissue;

bending the body of the suture device to juxtapose the distal and proximal portions externally of the tissue; and leaving the suture device in the tissue to be absorbed thereby.

8. A method of suturing a subcutaneous layer of skin adjacent an opening in skin having a subcutaneous layer and an outer layer, the method comprising the steps of providing a suture device made of bioabsorbable material having a body extending between a sharp distal end and a proximal end and configured to permit movement of the body of the suture device only forwardly through the subcutaneous layer of the skin;

penetrating an external surface of the subcutaneous layer of the skin on one side of the opening with the sharp distal end of the suture device, without penetrating the outer layer, to cause the body of the suture device to follow the sharp distal end into the subcutaneous layer and to move the proximal end of the suture device toward the subcutaneous layer;

moving the suture device forwardly to cause the sharp distal end to penetrate the subcutaneous layer of the skin on the other side of the opening and to cause the body of the suture device to follow the sharp distal end to approximate the sides of the opening;

penetrating the external surface of the subcutaneous layer on the other side of the opening to cause the sharp distal end of the suture device to exit the subcutaneous layer on the other side of the opening without penetrating the outer layer; and leaving the suture device in the subcutaneous layer to allow joining of the skin prior to absorption of the suture device.

9. A method of suturing a subcutaneous layer of skin as recited in claim 8 and further comprising the step of repeating said penetrating, moving and leaving steps to insert a plurality of the suture devices in successive alignment in the subcutaneous layer without penetrating the outer layer.

10. A method of suturing a subcutaneous layer of skin as recited in claim 8 wherein the suture device has a curved configuration and said moving step approximates the sides of the opening due to the curved configuration of the suture device.

11. A method of suturing a subcutaneous layer of skin as recited in claim 8 wherein the suture device has a straight configuration and said moving step approximates the sides of the opening as the suture device moves in a straight path.

12. A method of suturing tissue comprising the steps of providing a suture device made of bioabsorbable material having a curved body extending between a sharp distal end and a proximal end and configured to permit movement of the suture device only forwardly through the tissue;

penetrating an external wall of the tissue with the sharp distal end of the suture device to cause the suture device to enter the tissue;

advancing the suture device forwardly in a curved path into the tissue to cause the body and the proximal end of the suture device to follow the sharp distal end to position the body in the tissue;

penetrating the external wall of the tissue with the sharp distal end of the suture device to cause the sharp distal end to exit the tissue;

severing the sharp distal end from the remainder of the suture device immediately adjacent the external wall of the tissue; and leaving the remainder of the suture device in the tissue to be absorbed thereby.

* * * * *